(12) United States Patent
Daniell

(10) Patent No.: US 7,329,802 B1
(45) Date of Patent: Feb. 12, 2008

(54) GENETIC ENGINEERING OF COTTON TO INCREASE FIBER STRENGTH, WATER ABSORPTION AND DYE BINDING

(76) Inventor: Henry Daniell, 1255 Marina Point - #315, Casselberry, FL (US) 32707

( * ) Notice: Subject to any disclaimer, the term of this patent is extended or adjusted under 35 U.S.C. 154(b) by 0 days.

(21) Appl. No.: 09/251,638

(22) Filed: Feb. 17, 1999

Related U.S. Application Data

(60) Provisional application No. 60/074,997, filed on Feb. 17, 1998.

(51) Int. Cl.
*A01H 5/00* (2006.01)
*C12N 15/82* (2006.01)

(52) U.S. Cl. .................... 800/314; 435/320.1
(58) Field of Classification Search ......... 800/278, 800/288, 287, 314, 290; 536/23.1; 514/2; 439/468, 419; 435/320.1
See application file for complete search history.

(56) References Cited

U.S. PATENT DOCUMENTS 5,597,718 A * 1/1997 John et al. ............... 435/172.3
5,602,321 A * 2/1997 John ........................ 800/205
6,004,782 A * 12/1999 Daniell et al. ............ 435/71.2

OTHER PUBLICATIONS

John, M. E. and Keller, G. "Characterization of mRNA for a Proline-Rich Protein of Cotton Fiber." 1995, Plant Physiol., vol. 108, pp. 669-676.*
John, M. E. and Keller, G. "Metabolic pathway engineering in cotton: Biosynthesis of polyhydroxybutyrate in fiber cells." 1996, Proc. Natl. Acad. Sci. USA, vol. 93, pp. 12768-12773.*
Zhang, X. et al., "Expression of an environmentally friendly synthetic protein-based polymer gene in transgenic tobacco plants." 1996, Plant Cell Reports, vol. 16, pp. 174-179.*
Zhang, X. et al., "Nuclear Expression of an Environmentally Friendly Synthetic Protein Based Polymer Gene in Tobacco Cells." 1995, Biotechnology Letters, vol. 17, pp. 1279-1284.*
Urry et al, 1996, Protein-based polymeric materials (synthesis and properties), In: Polymeric Materials Encyclopedia, Salamone, JC, ed., CRC Press, Boca Raton, pp. 7263-7279.*
Daniell et al, 1997, Methods in Molecular Biology 63:359-371.*

* cited by examiner

*Primary Examiner*—Anne Kubelik
(74) *Attorney, Agent, or Firm*—Timothy H. Van Dyke; Beusse Wolter Sanks Mora & Maire

(57) ABSTRACT

An expression cassette having a fiber specific promoter driving expression of a gene encoding an elastic and plastic protein based polymer having the repetitive amino acid sequence Gly-Val-Gly-Val-Pro (SEQ. ID. NO. 2), a terminator, and selectable marker genes for transforming plant cells and a transgenic cotton plant having fiber cells stably transformed with the gene encoding the protein based polymer wherein the cotton fiber cells exhibit improved water absorption, temperature transition properties, fiber strength, elasticity, and dye binding capacity.

3 Claims, 3 Drawing Sheets

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Val Pro Gly Val Gly
1               5

<210> SEQ ID NO 2
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      Peptide

<400> SEQUENCE: 2

Gly Val Gly Val Pro
 1               5

<210> SEQ ID NO 3
<211> LENGTH: 50
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Val Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro
    50

<210> SEQ ID NO 4
<211> LENGTH: 100
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Val Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
                85                  90                  95

Val Gly Val Pro
            100

<210> SEQ ID NO 5
<211> LENGTH: 605
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: repeat_unit
<222> LOCATION: (1)..(605)
<223> OTHER INFORMATION: Repeats at least once

<400> SEQUENCE: 5

Gly Val Gly Val Pro Gly Val Gly Val Pro Gly Val Gly Val Pro Gly
```

-continued

```
 1               5                   10                  15
Val Gly Val Pro Gly Val Gly Val Pro Gly Val Gly Val Pro Gly Val
             20                  25                  30
Gly Val Pro Gly Val Gly Val Pro Gly Val Gly Val Pro Gly Val Gly
             35                  40                  45
Val Pro Gly Val Gly Val Pro Gly Val Gly Val Pro Gly Val Gly Val
             50                  55                  60
Pro Gly Val Gly Val Pro Gly Val Gly Val Pro Gly Val Gly Val Pro
 65                  70                  75                  80
Gly Val Gly Val Pro Gly Val Gly Val Pro Gly Val Gly Val Pro Gly
             85                  90                  95
Val Gly Val Pro Gly Val Gly Val Pro Gly Val Gly Val Pro Gly Val
             100                 105                 110
Gly Val Pro Gly Val Gly Val Pro Gly Val Gly Val Pro Gly Val Gly
             115                 120                 125
Val Pro Gly Val Gly Val Pro Gly Val Gly Val Pro Gly Val Gly Val
             130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
             165                 170                 175
Val Gly Val Pro Gly Val Gly Val Pro Gly Val Gly Val Pro Gly Val
             180                 185                 190
Gly Val Pro Gly Val Gly Val Pro Gly Val Gly Val Pro Gly Val Gly
             195                 200                 205
Val Pro Gly Val Gly Val Pro Gly Val Gly Val Pro Gly Val Gly Val
             210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
             245                 250                 255
Val Gly Val Pro Gly Val Gly Val Pro Gly Val Gly Val Pro Gly Val
             260                 265                 270
Gly Val Pro Gly Val Gly Val Pro Gly Val Gly Val Pro Gly Val Gly
             275                 280                 285
Val Pro Gly Val Gly Val Pro Gly Val Gly Val Pro Gly Val Gly Val
             290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
             325                 330                 335
Val Gly Val Pro Gly Val Gly Val Pro Gly Val Gly Val Pro Gly Val
             340                 345                 350
Gly Val Pro Gly Val Gly Val Pro Gly Val Gly Val Pro Gly Val Gly
             355                 360                 365
Val Pro Gly Val Gly Val Pro Gly Val Gly Val Pro Gly Val Gly Val
             370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
             405                 410                 415
Val Gly Val Pro Gly Val Gly Val Pro Gly Val Gly Val Pro Gly Val
             420                 425                 430
```

```
Gly Val Pro Gly Val Gly Val Pro Gly Val Gly Val Pro Gly Val Gly
            435                 440                 445
Val Pro Gly Val Gly Val Pro Gly Val Gly Val Pro Gly Val Gly Val
        450                 455                 460
Pro Gly Val Gly Val Pro Gly Val Gly Val Pro Gly Val Gly Val Pro
465                 470                 475                 480
Gly Val Gly Val Pro Gly Val Gly Val Pro Gly Val Gly Val Pro Gly
            485                 490                 495
Val Gly Val Pro Gly Val Gly Val Pro Gly Val Gly Val Pro Gly Val
        500                 505                 510
Gly Val Pro Gly Val Gly Val Pro Gly Val Gly Val Pro Gly Val Gly
            515                 520                 525
Val Pro Gly Val Gly Val Pro Gly Val Gly Val Pro Gly Val Gly Val
        530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
            565                 570                 575
Val Gly Val Pro Gly Val Gly Val Pro Gly Val Gly Val Pro Gly Val
        580                 585                 590
Gly Val Pro Gly Val Gly Val Pro Gly Val Gly Val Pro
            595                 600                 605

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Val Gly Phe Pro
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Gly Glu Gly Phe Pro
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gly Asp Gly Phe Pro
 1               5

<210> SEQ ID NO 9
<211> LENGTH: 39
```

-continued

```
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
gaggatccag gcgttggggt accgggtgtt ggcttcccg                              39

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
ctcctaggtc cgcaacccca tggcccacaa ccgaagggc                              39

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Val Gly Val Pro Gly Val Gly Phe Pro
 1               5                  10

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
ggtgamggtt tcccgggcgt tggtgtgccg                                        30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
ccactkccaa agggcccggc aaccacacgg c                                      31

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (2)
<223> OTHER INFORMATION: Asp or Glu

<400> SEQUENCE: 14

Gly Xaa Gly Phe Pro Gly Val Gly Val Pro
```

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
    Oligonucleotide

<400> SEQUENCE: 15
ggtgtaggct ttcgggtttc ggattcccag gcgttggatc cag                             43

<210> SEQ ID NO 16
<211> LENGTH: 53
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 16

Pro Gly Val Gly Val Pro Gly Val Gly Val Pro Gly Val Gly Val Pro
 1               5                  10                  15

Gly Val Gly Val Pro Gly Val Gly Val Pro Gly Val Gly Val Pro Gly
            20                  25                  30

Val Gly Val Pro Gly Val Gly Val Pro Gly Val Gly Val Pro Gly Val
         35                  40                  45

Gly Val Pro Gly Val
         50

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
    Oligonucleotide

<400> SEQUENCE: 17
cgggatccag gcgttggt                                                         18

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
    Oligonucleotide

<400> SEQUENCE: 18
ccacatccga aaggcccaaa gcctaagggt ccgcaaccta ggtc                             44

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 19

Gly Val Gly Phe Pro Gly Phe Gly Phe Pro
 1               5                  10

```
<210> SEQ ID NO 20
<211> LENGTH: 85
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
gttccgggtg ttggtgtacc gggtgttggt gtgccgggtg ttggtgttcc gggcgtaggc    60
gtaccgggcg taggcgtgcc gggcg                                         85

<210> SEQ ID NO 21
<211> LENGTH: 85
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
acctacaccc ggaacgccca cacccggcac gcccacgccc ggtacgccca cgcccggaac    60
gcctacgccc ggcacgccta cgccc                                         85

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
ccaggtgttg gatccg                                                   16
```

GENETIC ENGINEERING OF COTTON TO INCREASE FIBER STRENGTH, WATER ABSORPTION AND DYE BINDING

CROSS REFERENCE TO RELATED APPLICATION

This patent application benefits of the filing date of provisional application Ser. No. 60/074,997 filed Feb. 17, 1998, entitled Genetic Engineering of Cotton to Increase Fiber Strength, Water Absorption and Dye Binding. That earlier application is incorporated herein in its entirety.

FIELD OF THE INVENTION

The invention relates to genetic engineering of cotton to increase the cotton's fiber strength, water absorption and dye binding.

RELATED ART

A list of the related art is provided under the heading "Relevant Literature." All references cited herein are incorporated by reference.

BACKGROUND OF THE INVENTION

About 20 million metric tons of cotton fiber is produced annually worldwide with the U.S. producing about 20% of this. Approximately 16 million acres of cotton are planted in the U.S. representing one-seventh of the world acreage. The United States generates one fifth of the worldwide cotton fiber production, valued at about four billion dollars annually. Cotton is the premier natural fiber and provides excellent wearability and aesthetics. Although consumers prefer cotton, man-made fibers have captured a major share of the textile market while the market share of cotton is decreasing.

In order for the market share of cotton to increase, cotton fiber quality must be improved. Specifically, improvements in cotton fiber strength, the chemical reactivity for dye binding, water absorption and thermal properties are desirable for textile and other industrial applications. In the past, cotton fiber quality has been improved by classical plant breeding; however, this approach is seriously limited by species incompatibility and available traits. An alternative approach is to introduce foreign genes to confer desired traits into cotton via genetic engineering. Recently, John and Keller (1996) have reported expression of polyhydroxy butyrate polyester in cotton fiber, which has similar physical and chemical properties as polypropylene. This is the first report of a foreign gene expression in cotton fiber.

Cotton fiber or seed hair is a terminally differentiated single epidermal cell made up of primary and secondary cell walls, consisting primarily of cellulose (90%) and other compounds like hemicellulose, pectins and proteins. During the early stages of fiber development, the fiber cell elongates up to 3 cm over a period of 20 days post anthesis (DPA). The primary wall is about 100-200 molecules in thickness and consists of 30% cellulose and other polysaccharides, waxes and proteins (John and Keller, 1996). The secondary wall is made up of cellulose that is deposited during the third developmental stage, 16-45 DPA. Maturation of the fiber occurs 45-50 DPA, resulting in changes in mineral content and protein levels. The chemical composition and microstructure of primary and secondary walls influence properties like chemical reactivity, thermal characteristics, water absorption and fiber strength (John 1995b), which are important for the manufacturing of textile products. Therefore, it is highly desirable to synthesize a biopolymer within the fiber lumen without altering fiber wall integrity; this should result in sheltering the biopolymer within the cellulose walls (John and Keller, 1996).

We propose here to introduce a protein based polymer (PBP) from a synthetic gene into cotton that could increase fiber strength, alter thermal and water absorption qualities as well as enhance elasticity and dye binding capacity of cotton fiber.

SUMMARY OF THE INVENTION

PBPs are available in nature as materials with extraordinary mechanical properties, such as spider webs composed of silk threads tougher than steel and elastin, a rubber like classic fiber found in human arteries, that typically survives for more than 70 years, undergoing repeated cycles of stretching and relaxation. The PBP made from synthetic genes, encoding the amino acid sequence Val-Pro-Gly-Val-Gly (VPGVG) (SEQ. ID. NO. 1), typically found in elastin, exhibits elastic moduli that can range from $10^6$-$10^9$ dynes/$cm^2$ and temperature transition properties that enable water absorption 10 times its own weight. Therefore, the object of the invention is to introduce a PBP into cotton fiber to increase the fiber strength, water absorption, thermal characteristics and dye binding. In this project, we attempt to genetically engineer cotton fiber with a PBP gene encoding the amino acid sequence Gly-Val-Gly-Val-Pro (GVGVP) (SEQ. ID. NO. 2).

We propose here to introduce a protein based polymer (PBP) encoded by a synthetic gene into cotton to increase fiber strength, alter thermal and water absorption qualities, and enhance the elasticity and dye binding capacity of cotton fiber. Specifically, we propose the development of recombinant DNA transformation vectors or expression cassettes for enhanced protein polymer expression in cotton fiber and of transgenic cotton plants having such expression cassettes. We further propose assaying transgenic expression using molecular and biochemical methods in addition to assaying fiber qualities of control and transgenic plants using physical and chemical testing, including fiber strength, elongation, water absorption and dyeability and analyzing the genetic composition of the transgenic plants.

DETAILED DESCRIPTION OF THE INVENTION

Figure 1:
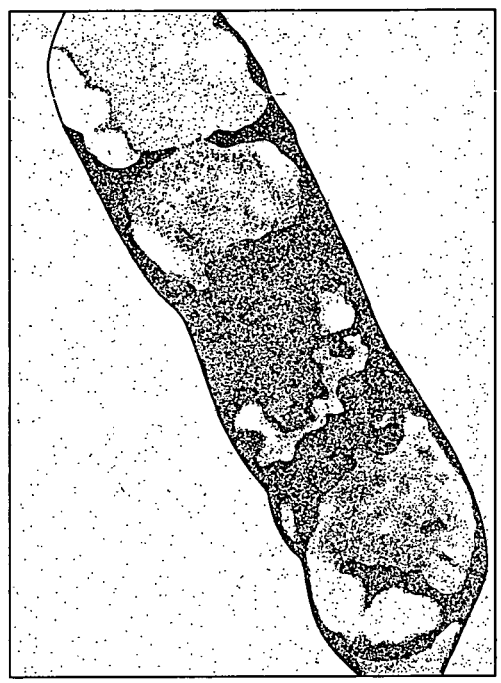
FIG. 1 shows expression of PBP in *E. coli*.

PBPs are available in nature as materials with extraordinary mechanical properties, such as spider webs composed of silk threads tougher than steel, elastin fibers in the mammalian cardiovasculature which can last almost a century without loss of function and the adhesive produced by a mussel's foot which consistently adheres under extreme conditions in salt water. Elastin, a rubber like elastic fiber found in human arteries (especially in the aortic arch) typically survives for more than 70 years, undergoing repeated cycles of stretching and relaxation. The pentamer peptide sequence Val-Pro-Gly-Val-Gly (VPGVG) is typical of all sequenced mammalian elastin proteins, and in bovine elastin, this sequence is repeated eleven times without a single substitution. It has been shown that this elastic and plastic PBP exhibits elastic moduli that can range from $10^6$-$10^9$ dynes/cm$^2$.

The remarkable elastic properties of PBPs containing multiple repeats of the pentamer sequence (Val$^1$-Pro$^2$-Gly$^3$-Val$^4$-Gly$^5$) (SEQ. ID. NO. 1), qualify their use as bioelastic materials (Urry, 1995). Elastic and plastic PBPs offer a range of materials similar to that of oil-based polymers, such as hydrogels, elastomers and plastics. PBPs of varied design and composition can be prepared and made biodegradable with chemical clocks to program their half lives (Urry, 1995). Additionally, PBPs exhibit remarkable biocompatibility, thereby enabling their use in a whole range of medical applications including the prevention of post-surgical adhesions, tissue reconstruction and programmed drug delivery (Urry et al. 1993). For instance, the polymer poly (GVGVP) (SEQ. ID. NO. 2) has been successfully used to prevent adhesions in the rat contaminated peritoneal model following abdominal injury (Urry et al., 1993). The non-medical application of these materials include biodegradable plastics, transducers, molecular machines, superadsorbant agents, and controlled release of agricultural crop enhancement agents, such as pesticides, growth factors, and fertilizers (Daniell, 1995). Biodegradable plastics made from PBPs may not only break down in the environment but can become a useful part of the environment. Since saline solution can breakdown PBPs, the plastic PBP products can be disposed in oceans and gulfs; as they degrade, the plastics can provide proteins for oceanic animals, thus entering the food chain and benefiting the marine ecosystem.

PBPs also exhibit temperature transition properties; parts of the polymer are hydrophobic and others are hydrophilic and water molecules accordingly arrange themselves around these sections of the molecules in different configurations. The relative stability of these configurations changes with temperature and so does the preferred shape of the protein. For example, when genetically engineered cotton containing the PBP is worn by an individual, the polymer will experience an inverse temperature transition just below the normal temperature of skin. When liquid touches the inside surface of clothing, the polymer molecules will soak it up, but they would remain in the folded state. The polymer chains' propensity to unfold at lower temperatures will spontaneously wick fluid away from the warm body and toward the cool outer surface of the clothing. Thus, this polymer can absorb 10 times its own weight in water (Urry, 1995). Moisture and water uptake by textile fibers are very important in regard to dyeing and finishing as well as for comfort and wearability. Water acts as a vehicle in the pores of the cellulose fiber for transport of dyes and other chemicals. Water absorption is directly correlated with fiber dyeability; reactive dyes form non-covalent bonds with functional groups along the polymer backbone (Rivlin, 1992). Dye binding capacity will be enhanced by increased protein content of the fiber; expression of the PBP in cotton fiber will significantly increase the fiber protein content.

Figure 2:
FIG. 2 shows expression of PBP in a plant cell.

The gene encoding poly(GVGVP)$_{121}$(SEQ. ID. NO. 5) has been expressed in different systems including bacteria (Daniell, 1995; Guda et al., 1995; Daniell et al., 1997; Urry et al., 1995), fungi (Herzog et al., 1997) and tobacco plants (Zhang et al., 1995, 1996; Daniell 1995; Daniell and Guda, 1997). Following expression of a small, 100 amino acid polypeptide (GVGVP)$_{20}$ (SEQ. ID. NO. 4) in E. coli (McPherson et al., 1992), larger versions of the same polypeptide (GVGVP) (SEQ. ID. NO. 2) containing 121 repeats (605 amino acids) or 251 repeats (1255 amino acids) were hyperexpressed in E. coli (Guda et al., 1995; Brixey et al., 1997). Bacterial cells showed polymer inclusion bodies occupying up to 90% of their cell volume under optimal conditions (See FIG. 1). Production of polymers by fermentation, however, is not cost effective when compared with petroleum based polymers. Therefore, we have recently expressed the GVGVP (SEQ. ID. NO. 2) 120mer in tobacco. Even though lower levels of expression were observed in cultured tobacco cells (Zhang et al., 1995) and some transgenic plants in the F0 generation (probably due to the position effect and heterozygous nature, Zhang et al., 1996), higher levels of polymer expression were observed in transgenic plants after self-crossing in the F1 generation; inclusion bodies have been observed in tobacco cells (see FIG. 2), which is a good indication of a very high level of PBP expression (Daniell, 1995; Daniell and Guda, 1997). The transgenic tobacco plants expressing this PBP grew, flowered and produced seeds normally (Zhang et al., 1996). Physiological and ultrastructural studies reveal that transgenic tobacco plants expressing PBP are similar to control untransformed plants.

What is required for the commercial viability of protein-based polymers is a cost of production that would begin to rival that of petroleum-based polymers. The potential to do so resides in low cost bioproduction. We have recently demonstrated a dramatic hyperexpression of an elastin protein-based polymer, (Gly-Val-Gly-Val-Pro (SEQ ID NO. 2))$_n$ or poly(Gly-Val-Gly-Val-Pro) (SEQ ID NO:2), which is a parent polymer for a diverse set of polymers that exhibit inverse temperature transitions of hydrophobic folding, and assembly as the temperature is raised through a transition range and which can exist in hydrogel, elastic and plastic states. Electron micrographs revealed formation of inclusion bodies in E. coli cells occupying up to 80-90% of the cell volume under optimal growth conditions (3a). The beauty of this approach is the lack of any need for extraneous sequences for the purposes of purification (4) or adequate expression. The usual strategy for expression of a foreign protein or protein-based polymer in an organism such as E. coli anticipates that the foreign protein will be injurious to the organism. Accordingly, the transformed cells are grown up to an appropriate stage before expression of the foreign protein is begun and expression is generally considered viable for only a few hours. The situation is quite different for the elastic protein-based polymer considered here. This may result in part due to the extraordinary biocompatibility exhibited by (Gly-Val-Gly-Val-Pro, (SEQ ID NO:2))$_n$ and its related polymers. The elastic protein-based polymer, (Gly-Val-Gly-Val-Pro, (SEQ ID NO:2))$_n$ and its γ-irradiation crosslinked matrix as well as related polymers and matrices appear to be ignored by a range of animal cells and by tissues of the whole animal (5-7).

Construction of a synthetic protein-based polymer gene: As an illustration of an uninduced hyper-expression of a protein-based polymer in E. Coli, we have chosen a gene encoding 121 repeats of the elastomeric pentapeptide-gly-val-gly-val-pro (SEQ ID NO:2). This gene, (gly-val-gly-val-pro)$_{121}$, was constructed by ligase concatenation of DNA sequence encoding (gly-val-gly-val-pro)$_{10}$ and isolation of a concatener having 12 repeats of this monomer gene plus an additional C-terminal (gly-val-gly-val-pro) sequence encoded by a 3' cloning adaptor. The gene encoding (gly-val-gly-val-pro)$_{10}$ was synthesized and cloned into a multi-purpose cloning plasmid from which it was then excised by digestion at flanking sites with the restriction endonuclease Pf1M1. A substantial amount of the Pf1M1 gene fragment was purified and self-ligated in the presence of limited amounts of synthetic double-stranded oligonucleotide adapters that provided the additional restriction sites needed for cloning the resulting concatemers. Pf1M1 cleaves at its recognition site in the DNA to leave two single-stranded extensions that are not self-complementary (i.e., nonpalindromic) but are only complementary to each other, therefore proper translational polarity is maintained by head-to-tail tandem coupling of the monomer gene unites by ligase during the concatenation reaction.

Pro gly val gly val pro (Gly-Val-Gly-Val-Pro)8 gly val gly val pro gly val (SEQ ID NO. 16)

Where nucleotides M/k=A/t when amino acid X=E and M/k=C/g when X=D. For each gene, two single-stranded oligonucleotides, indicated by the upper-case letters in the sequence, where annealed through their overlapping regions of complementarily (dashed line) and extended from their 3' ends with DNA polymerase and deoxynucleotide-triphosphates to give the full-length, double-stranded molecule.

The initial gene which encodes 10 repeating unites of the elastomeric pentapeptide gly-val-gly-val-pro (SEQ ID NO. 2), i.e. (gly-val-gly-val-pro)$_{10}$ (SEQ ID NO. 3) was constructed by using polymerase chain reaction (McPherson et al. 1992). Higher molecular weight polymer genes were then

```
cgggatCCA GGC GTT GGT (SEQ ID NO. 17)------------------------CCA GGT GTT Ggatccg (SEQ ID NO. 22)
BamH1     Pf1M1                                                 Pf1M1 BamH1
```

Above is the amino acid sequence and flanking restriction endonuclease sites of the basic polymer building block coding for (gly-val-gly-val-pro, (SEQ ID NO:3))$_{10}$. Using synthetic oligonucleotides and PCR, (gly-val-gly-val-pro, (SEQ ID NO:3))$_{10}$ was amplified with flanking BamH1 and Pf1M1 ends and the 121-mer gene was inserted into a pUC118 as a BamH1 fragment. For expression under control of the T7 polymerase gene promoter, a 121-mer gene was created by concatenation of the Pf1M1 10-mer fragment with terminal cloning adaptors and subsequently inserted into the expression vector pET-11d.

Genes for the tricosapeptides gly-val-gly-val-pro (SEQ ID NO. 2) gly-val-gly-phe-pro (SEQ ID NO. 6) gly-glu-gly-phe-pro (SEQ ID NO. 7) gly-val-gly-val-pro (SEQ ID NO. 2) gly-val-gly-phe-pro (SEQ ID NO. 6) gly-phe-gly-phe-pro and gly-val-gly-val-pro (SEQ ID NO. 14) gly-val-gly-phe-pro (SEQ ID NO. 6) gly-asp-gly-phe-pro (SEQ ID NO. 8) gly-val-gly-val-pro (SEQ ID NO. 2) gly-val-gly-phe-pro (SEQ ID NO. 6) gly-phe-gly-phe-pro, analogous to compounds LXII and LIX, respectively, were constructed using synthetic oligonucleotides. The double-stranded DNA sequence of these genes with the corresponding amino acid sequence is the following (Equation 1):

```
                                                   (SEQ ID NO. 9)
   BamH-1    Pf1M-1
   5'-GAGGATCCAGGCGTTGGGGTACCGGGTGTTGGCTTCCCG
```

3'-ctcctaggtccgcaacccatggcccacaaccgaagggc (SEQ ID NO. 10)

Gly val gly val pro gly val gly phe pro (SEQ ID NO. 11)

GGTGAMGGTTTCCCGGGCGTTGGTGTGccg (SEQ ID NO. 12)

ccactkcCAAAGGGCCCGGCAACCACACGGC (SEQ ID NO. 13)

Gly X gly phe pro gly val gly val pro (SEQ ID NO. 14)
                                    Pf1M-1        BamH-1 ggtgtaggctttcgggtcggattcccaggcgttggatccag-3' (SEQ ID NO. 15)

CCACATCCGAAAGGCCCAAAGC-CTAAGGGTCCGCAACCTAGGTC-5'(SEQ ID NO. 18)

gly val gly phe pro gly phe gly phe pro (SEQ ID NO. 19)

made by concatenation/ligation reaction using suitable adaptor oligonucleotide fragments. Details of a series of these gene constructs have been published elsewhere (McPherson et al. 1996). These higher molecular weight polymer genes were subsequently cloned into pUC118 as a BamH1-BamH1 fragment.

Synthetic Oligonucleotides

The universal sequencing primer was obtained from New England Biolabs. All other oligonucleotides either were synthesized on an Applied Biosystems automated DNA synthesizer by the University of Alabama at Birmingham Cancer Center DNA Synthesis Core Facility or were purchased from Oligos, Etc.

Construction of Synthetic Gene

A DNA sequence coding for (VPGVG SEQ ID NO. 1)$_{10}$ was constructed using two synthetic oligonucleotides, each 85 bases in length, with 3'-overlapping complementary ends. They had the following sequences:

5'-GTTCCGGGTGTTGGTGTACCGGGTGTTG-GTGTGCCGGGTGTTGGTGTTCCGGGC GTAGGCG-TACCGGGCGTAGGCGTGCCGGGCG-3' (SEQ ID NO. 20)

5'-ACCTACACCCGGAACGCCCACACCCG-GCACGCCCACGCCCGGTACGCCCACGCC CGGAACGCCTACGCCCGGCACGCCTACGCCC-3' (SEQ ID NO. 21)

Briefly, the 3' ends were annealed through a 20-base region of complementarity and extended with AMV reverse transcriptase and deoxynucleotides to provide complementary strands of 150 bases.

Polymerase Chain Reaction (PCR)

PCR (Saiki et al., 1987) reactions were performed in a total volume of 100 µL containing approximately 1 ng of plasmid DNA as template and 100 pmol of each primer in a mixture of 10 mM Tris-HCl, pH 8.3, 50 mM KCl, 1.5 mM MgCl$_2$, 200 mM each deoxynucleotidetriphosphate, and 2.5 unites of recombinant *Thermus aguaticus* DNA polymerase (Amplitaq, Perkin-Elmer Cetus). The above mix was overlaid with an equal volume of mineral oil (reagent-grade, Sigma) and subjected to 30 cycles of 94° C. for 1 min, 52° C. for 3 min, and 72° C. for 3 min in a Perkin-Elmer Cetus DNA thermal cycler, with minimal ramp time between steps. In each case, a DNA fragment of the desired size was purified by first digesting the PCR product with the appropriate restriction enzymes, followed by electrophoresis through 6% acrylamide, band excision, electroelution into dialysis tubing, and precipitation with ethanol.

In this context it should be pointed out that Agracetus, Inc. recently has introduced the polyhydroxybutyrate polymer biosynthetic genes into cotton for polyester expression in fiber (John and Keller, 1996). However, their genetic engineering approach, in addition to introducing a group of genes for the entire pathway, is limited by low levels of required intermediates (such as acetyl CoA) in the cytosol (Nawrath et al. 1995) resulting in very low levels of expression (0.3% fiber weight, John and Keller, 1996). Furthermore, properties of this polyester can not be modified to suitably alter fiber quality because the polyester is an end product of a bacterial pathway.

In contrast we attempt here to express a protein polymer and not a polyester. PBPs used in our study are expressed from a single synthetic gene that can easily be altered to increase the fiber strength, water absorption, thermal properties, elasticity and dye binding capacity of cotton fiber by changing the amino acid composition. We attempt to accomplish this using a gene encoding $GVGVP_{121}$(SEQ. ID. NO. 2); this gene has been expressed at high levels in bacteria (FIG. 1; Daniell et al., 1997) and tobacco plants (FIG. 2; Daniell and Guda, 1997). Transgenic tobacco plants expressing this PBP grew, flowered and produced seeds normally (Zhang et al., 1996). However, this gene has not previously been expressed in cotton fibers.

Recombinant DNA Vectors for PBP Gene Expression in Cotton Fiber

Figure 3:
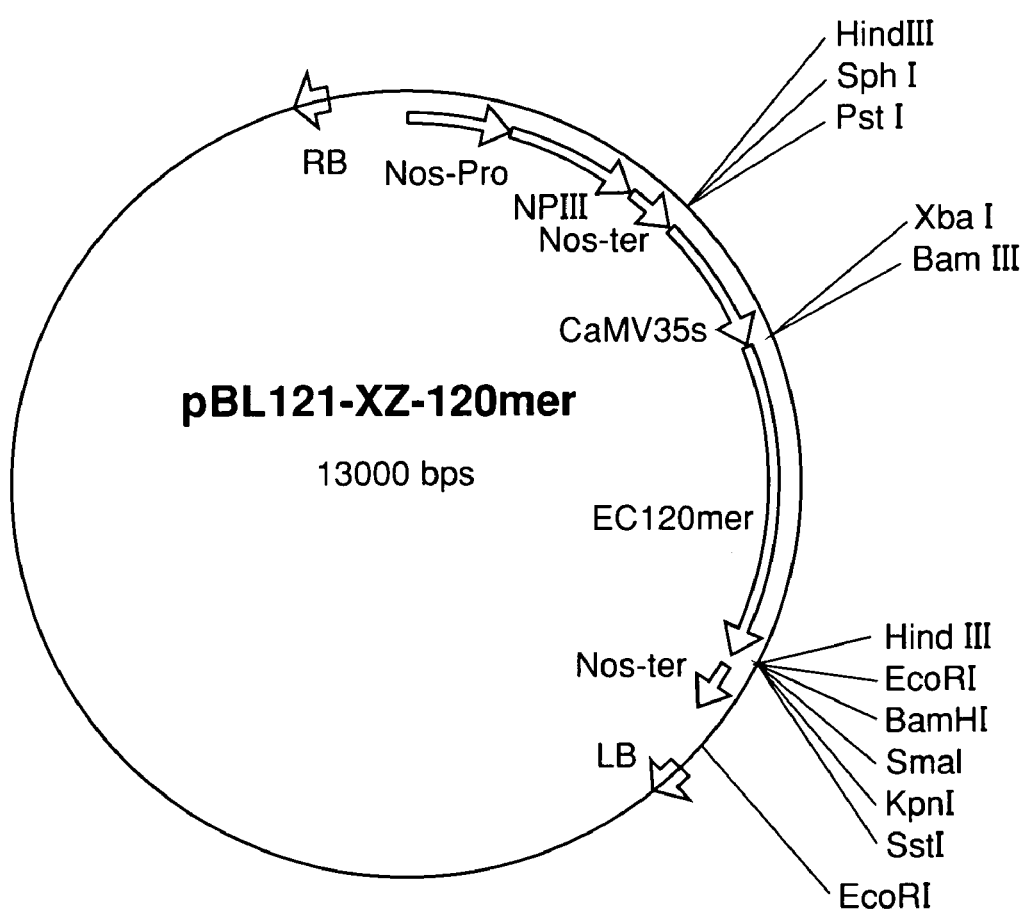
FIG. 3 illustrates the plasmid map of pBI121-XZ-120mer.

A nuclear vector for transient expression of the 120mer gene has been constructed. The plasmid pUC-GUS (obtained from Stratagene) was digested with XbaI and SstI to remove the 1.8 kb XbaI-SstI fragment containing the uidA gene, and the remaining 4.3 kb fragment was ligated with the 1.8 kb 120mer polymer fragment (obtained as XbaI-SstI fragment in pUC118) to produce plasmid pUC-XZ-120mer. The 120mer polymer gene in this construct is driven by the CaMV 35S promoter and flanked by the nos terminator. A nuclear vector for stable expression of the 120mer polymer protein also has been constructed. The uidA gene was removed from the plasmid pBI121 as a XbaI-SstI fragment and replaced by the 120mer polymer fragment (obtained as XbaI-SstI fragment in pUC118 plasmid) resulting in the construct pBI121-XZ-120mer (FIG. 3). The 120mer polymer gene in this construct is driven by the CaMV 35S promoter and flanked by the nos terminator. This nuclear vector also contains a nptII gene driven by the nos promoter and flanked by the nos terminator to facilitate selection of transformed cells or tissues on kanamycin. In stably transformed tobacco plants a 1.8 kbp EG-120mer polymer gene fragment was found to be integrated into the tobacco nuclear genome. A 1.8 kbp EG-120mer polymer gene transcript was observed in Northern blots. Gels stained with $CuCl_2$ show the presence of polymer and Western blots confirm the identity of the polymer protein (Zhang et al., 1995, 1996). Even though lower levels of expression were observed in cultured tobacco cells (Zhang et al., 1995) and some transgenic plants in the F0 generation probably due to the position effect and heterozygous nature, Zhang et al., 1996), higher levels of polymer expression were observed in tobacco cells (see FIG. 2); this is a good indication of a PBP express (Daniell, 1995; Daniell and Guda, 1997). Transgenic tobacco plants expressing the PBP grew, flowered and produced seeds normall (Zhang et al., 1996). Physiological and ultrastructural studies reveal that transgenic tobacco plants expressing PBP are similar to control untransformed plants.

While the levels of PBP expression are sufficient in transgenic plants, we are attempting to further enhance the level of polymer production by modifying the codon composition. Therefore, the plant expression vector pBI-EV35S-130mer, with a plant nuclear preferred codon composition gene sequence, coding for the same polymer protein has been constructed in our lab and introduced into transgenic tobacco plants. Characterization of the tobacco transgenic plants expressing the 130mer polymer protein is in progress.

Figure 4:
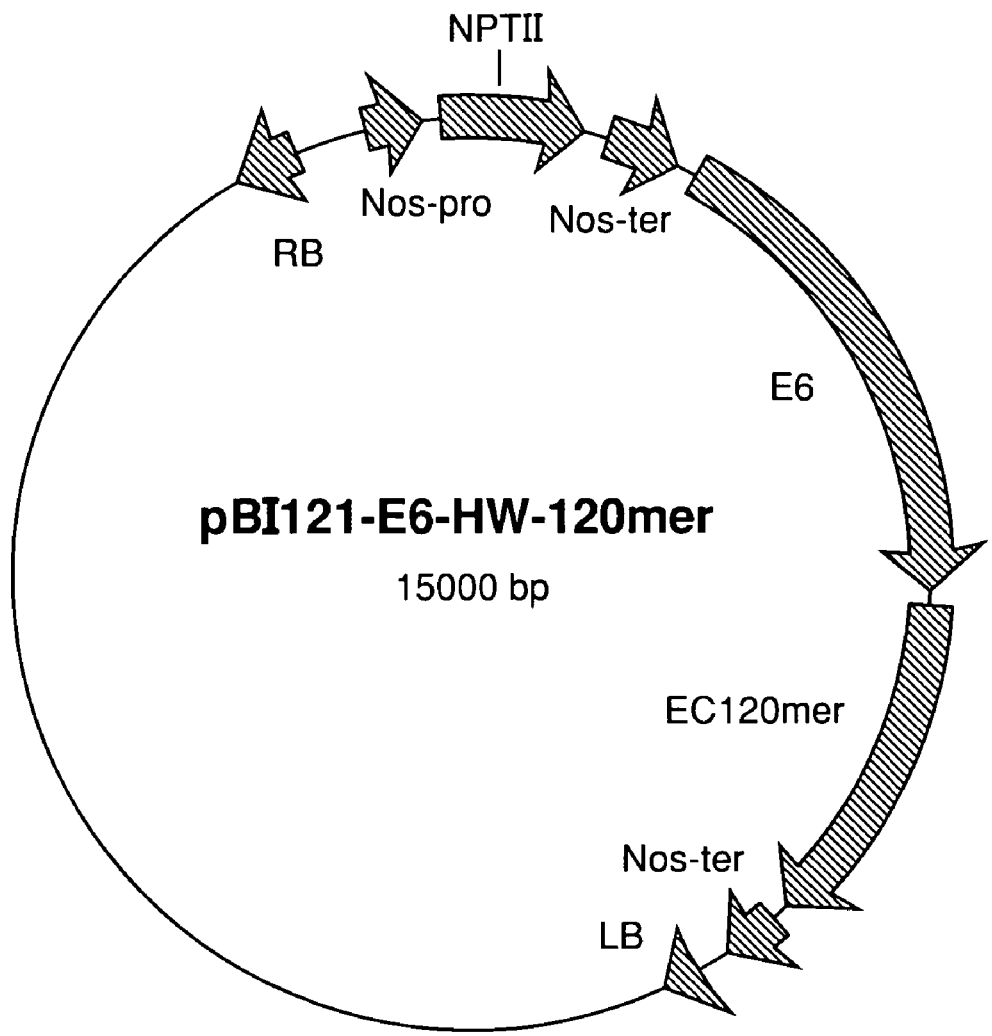
FIG. 4 illustrates the plasmid map of pBI121-E6-HW-120mer.

Identified fiber genes can be grouped into two types— genes which only express in fibers (fiber-specific genes) and those which express in other tissue types besides fibers. Fiber-specific genes, isolated from cDNA libraries, include a lipid transfer protein gene, the "fiber" gene E6 and Rac 13. However, only the promoter for the E6 gene, isolated from a genomic library, has been well characterized (John, 1995a). In order to avoid possible pleiotropic or epistatic effects of introduced genes, it is desirable to use promoters which will express foreign genes primarily in fiber cells. Therefore, in order to express PBP genes in cotton fibers, the 35S CaMV promoter in recombinant constructs (pBI121-XZ-120mer and pBI-EV35S130mer) is replaced by the E-6 promoter (FIG. 4); this will direct expression of foreign genes in a tissue specific and developmentally regulated manner in transgenic cotton plants (John and Crow, 1992). The E6 promoter has been used successfully to express PHB polymers in cotton fiber (John and Keller, 1996).

Cotton Transformation with PBP Genes

Several methods for transformation of cotton in addition to *Agrobacterium*-mediated transformation of hypocotyls have been described, including particle bombardment of embryogenic cultures and shoot apical meristems, followed by somatic embryogensis or shoot formation from apical tissues, respectively. However, the *Agrobacterium*-mediated method followed by somatic embryogenesis (Trolinder and Goodin, 1987, 1988) remains the most reliable and manageable method in the university setting. In contrast, in the alternative method of particle bombardment (Daniell, 1997) of shoot apical meristems (McCabe and Martinell, 1993), thousands of bombardment events and repeated pruning of the resulting chimeric seedlings are required to produce uniform plants with transformed epidermal tissue or germ lines (John and Keller, 1996). The technical demands of the work are too great to be accomplished by the number of employees commonly supported in academic laboratories.

Alternatively, the *Agrobacterium*-mediated method is manageable in the university setting and has been used successfully to introduce 2,4-D resistance into cotton (Bayley et al., 1992). However, a disadvantage of this technique is that the subsequent regeneration is not cultivar-independent (Trolinder and Goodin, 1987, 1988). Consequently, desirable traits in the transformed plants must be subsequently crossed into current production varieties, such as *Gossypium hirsutum* L. var Coker 312 and 5110, T25, Y169, Paymaster 303, Paymaster 784 and RQSX-1-1, the *G. hirsutum* x *G. barbadense* hybrid. After completion of recombinant DNA vector constructions, cotton transformation will be carried out in Dr. Haigler's laboratory (Texas Tech, Lubbock, Tex.). Fiber qualities of genetically engineered cotton will be analyzed at Auburn University and in collaboration with Dr. Rajasckaran, (USDA Southern Regional Laboratories, New Orleans, La.).

RELEVANT LITERATURE

Bayley, C., N. L. Trolinder, C. Ray, M. Morgan, J. E. Quissenbury, and D. W. Owen. 1992. Engineering 2,4-D resistance in cotton. Theor. Appl. Genet. 83:645-649.

Brixey, J., C. Guda and H. Daniell. 1997. The chloroplast psbA promoter is more efficient in E. coli than the T7 promoter for hyper expression of a foreign protein. Biotechnology Letters 19: 395-400.

Daniell, H. 1995. Producing polymers in plants and bacteria. Inform 6: 1365-1370.

Daniell, H. 1997. Transformation and foreign gene expression in plants mediated by microprojectile bombardment. Methods in Molecular Biology 62: 463-490.

Daniell, H. and C. Guda. 1997. Biopolymer production in microorganisms and plants. Chemistry and Industry, 14: 555-560.

Daniell, H., C. Guda, X. Zhang, D. McPherson, D. W. Urry. 1997. Hyperexpression of a synthetic protein based polymer gene. Methods in Molecular Biology 63: 359-371.

Guda, C., X. Zhang, D. T. McPherson, J. Xu, D. W. Urry and H. Daniell. 1995. Hyper-expression of an environmentally friendly synthetic polymer gene. Biotechnology Letters 17: 745-750.

Herzog, R. W., Singh, N. K., Urry, D. W., & Daniell, H. 1997. Synthesis of a protein based polymer (elastomer) gene in *Aspergillus nidulans*. Applied Microbiology & Biotechnology 47: 368-372.

John, M. E. 1995a. Characterization of a cotton (*Gossypium hirsutum* L.) Fiber mRNA (Fb-B6). Plant Physiol. 107: 1477-1478.

John, M. E. 1995b. Prospects for modification of fibers through genetic engineering of cotton. Industrial Biotechnological Polymers, Chapter 6, Pp. 69-79.

John, M. E. and L. J. Crow, 1992. Gene expression in cotton fiber: Cloning of the mRNAs. Proc. Natl. Acad. Sci. USA. 89: 5769-5773.

John, M. E. and G. Keller. 1995. Characterization of mRNA for a proline-rich protein of cotton fiber. Plant Physiol. 108: 669-676.

John, M. E. and G. Keller. 1996. Metabolic pathway engineering in cotton: Biosynthesis of polyhydroxybutyrate in fiber cells. Proc. Natl. Acad. Sci. USA 93: 12768-12773.

McPherson, D. T., Morrow, C., Mincham, D. J., Wu, J., Hunter, E., & Urry, D. W. 1992. Production and purification of a recombinant elstomeric polypeptide from E. coli. Biotechnol. Prog. 8, 347-52.

McCabe, D. E. and B. J. Martinell. 1993. Transformation of elite cotton cultivars via particle bombardment of meristems. Bio/Technology 11: 596-598.

Nawrath, C., Y. Poirier, and C. Somerville. 1995. Plant polymers for biodegradable plastics: Cellulose, starch and polyhydroxyalkonates. Molecular Breeding 1: 105-122.

Rivlin, J. 1992. The Dyeing of Textile Fibers: Theory and Practice. Philadelphia College of Textiles and Sciences, Philadelphia, Pa.

Trolinder, N. L. and J. R. Goodin. 1988. Somatic embryogenesis in cotton (Gossypium) II. Requirements for embryo development and plant regeneration. Pl. Cell, Tissue Org. Cult. 12: 43-53.

Trolinder, N. L. and J. R. Goodin. 1987. Somatic embryogenesis and plant regeneration in cotton (*Gossypium hirsutum* L.) Plant Cell Reports 6: 231-234.

Urry, D. W. 1995. Elastic biomolecular machines. Scientific American 272: 64-69.

Urry, D. W., D. T. McPherson, J. Xu, H. Daniell, C. Guda, D. C. Gowda, N. Jing, and T. M. Parker. 1995. Protein based polymeric materials: Synthesis and Properties. Pp. 2645-2699. In: The Polymeric Materials Encyclopedia: Synthesis, Properties and Applications. Salamone, J. C. (ed.) CRC press.

Urry, D. W., Nicol, A. Gowda, D. C., Hoban, L. D., McKee, A., Williams, T., Olsen D. B., & Cox, B. A. 1993. Medical applications of bioelastic materials, in Biotechnological Polymers: Medical, Pharmaceutical and Industrial Applications, (Ed. C. G. Gebelein) Atlanta: Technomic Publishing Co., Inc., 82-103.

Zhang, X., C. Guda, R. Datta, R. Dute, D. W. Urry, and H. Daniell. 1995. Nuclear expression of an environmentally friendly synthetic protein based polymer gene in tobacco cells. Biotechnology Letters 17: 1279-1284.

Zhang, X., D. W. Urry, and H. Daniell. 1996. Expression of an environmentally friendly synthetic protein based polymer gene in transgenic tobacco plants. Plant Cell Reports 16: 174-179.

---

The invention claimed is:

1. A transgenic cotton plant comprising fiber cells stably transformed with an expression cassette encoding 120, 121 or 130 repeats of the amino acid sequence Gly-Val-Gly-Val-Pro (SEQ ID NO:2).

2. An expression cassette comprising one or more regulatory elements, one or more selectable marker genes, a fiber specific promoter operably linked to a nucleic acid encoding 120, 121 or 130 repeats of the amino acid sequence Gly-Val-Gly-Val-Pro (SEQ ID NO:2) and a terminator.

3. The expression cassette of claim 2, wherein said fiber specific promoter is an E-6 promoter.

* * * * *